United States Patent [19]

Givens et al.

[11] Patent Number: 5,093,623
[45] Date of Patent: Mar. 3, 1992

[54] METHOD FOR DETERMINING ELECTRICAL ANISOTROPHY FROM RADIAL RESISTIVITIES IN CYLINDRICAL CORE SAMPLES OF POROUS ROCK

[75] Inventors: Wyatt W. Givens, Dallas; W. David Kennedy, Carrollton, both of Tex.

[73] Assignee: Mobil Oil Corporation, Fairfax, Va.

[21] Appl. No.: 671,249

[22] Filed: Mar. 19, 1991

[51] Int. Cl.$^5$ ............................................. G01V 3/02
[52] U.S. Cl. ...................................... 324/376; 73/153
[58] Field of Search .................... 324/376; 73/151, 153

[56] References Cited

U.S. PATENT DOCUMENTS

| | | | |
|---|---|---|---|
| 2,802,172 | 8/1957 | Mueller et al. | 324/376 |
| 4,628,267 | 12/1986 | Lee et al. | 324/376 |
| 4,686,477 | 8/1987 | Givens et al. | 324/376 X |
| 4,907,448 | 3/1990 | Givens | 324/376 |
| 4,924,187 | 5/1990 | Sprunt et al. | 324/376 |
| 4,926,128 | 5/1990 | Givens | 324/376 |

FOREIGN PATENT DOCUMENTS 510561 3/1955 Canada .................................. 324/376

OTHER PUBLICATIONS

Marinelli et al, "Core Tester Contact Assembly", *IBM/TDB*, vol. 9, No. 3, Aug. 1966, pp. 296-297.

*Primary Examiner*—Kenneth A. Wieder
*Assistant Examiner*—Warren S. Edmonds
*Attorney, Agent, or Firm*—Alexander J. McKillop; Charles J. Speciale; George W. Hager, Jr.

[57] ABSTRACT

A cylindrical core sample of a subterranean formation is fluid saturated and subjected to a confining pressure. Voltages are measured in a plurality of directions through the core sample which are normal to the cylindrical axis of the core sample at a plurality of spaced-apart positions along such axis and utilized to determine resistivities. These resistivities are compared to identify the radial direction of any electrical anisotropy in the core sample for differing fluid saturation conditions.

8 Claims, 2 Drawing Sheets

METHOD FOR DETERMINING ELECTRICAL ANISOTROPHY FROM RADIAL RESISTIVITIES IN CYLINDRICAL CORE SAMPLES OF POROUS ROCK

BACKGROUND OF THE INVENTION

This invention relates to the area of oil and natural gas exploration and, more particularly, to a method for identifying regions of rock formations from which hydrocarbons may be produced.

Hydrocarbon saturation $S_o$ is generally determined from water saturation $S_w$ as follows:

$$S_o = 1 - S_w. \tag{1}$$

Water saturation present in a subterranean formation is typically determined from interpretation of conventional electrical (i.e., resistivity) logs recorded in a borehole drilled through the formation. Water saturation of the available pore space of the formation is determined from the resistivity log measurements using the Archie equation set forth in "The Electrical Resistivity Log As An Aid In Determining Some Reservoir Characteristics", Trans. AIME, Vol. 46, pp. 54-62, 1942, by G. E. Archie. This equation is expressed as follows:

$$S_w{}^n = R_w/\phi^m R_t, \tag{2}$$

where $S_w$ is the fractional water saturation (i.e. free and bound water of the formation expressed as a percent of the available pore space of the formation, $R_w$ is the formation water resistivity, $\phi$ is the formation porosity, $R_t$ is the formation electrical resistivity, n is the saturation exponent and m is the porosity or cementation exponent. The Archie equation may be expressed in other ways and there are numerous methods in the art for determining, measuring or otherwise obtaining the various components needed to predict fractional water saturation $S_w$ from the formation resistivity, $R_t$, using the equation in any of its forms.

Archie defined two quantities that provided the basis for his water saturation equation (1). The first quantity is the formation factor F which defines the effect of the rock matrix on the resistivity of water as follows:

$$F = R_o/R_w, \tag{3}$$

where
$R_o$ = resistivity of water saturated rock and
$R_w$ = water resistivity.

Archie reasoned that for a given value $R_w$, the formation factor F would decrease with increasing porosity, $\phi$, to some exponent m:

$$F = 1/\phi^m. \tag{4}$$

This porosity exponent m has also become known as the Archie cementation exponent. Thus Archie provided a useful characterization of a rock fully saturated with a conducting brine in terms of the water resistivity $R_w$, porosity $\phi$, and a rock parameter m. It is important to note that Archie assumed all conductance to be in the brine.

The second quantity is the resistivity index I defined as the ratio of the resistivity of a rock partially saturated with water and hydrocarbon, $R_t$, to the same rock saturated fully with water, $R_o$, as follows:

$$I = R_t/R_o. \tag{5}$$

Archie reasoned that as the water saturation decreased (i.e. hydrocarbon saturation increased) the resistivity $R_t$ and hence I would increase to some exponent n:

$$I = 1/S_w{}^n \tag{6}$$

where $S_w$ = volume of water in pores/total pore volume. This exponent n has become known as the Archie saturation exponent. It is again important to note that Archie assumed all conductance to be in the brine and further that all pores within the rock have the same water saturation $S_w$.

It is these two equations (4) and (6) for the formation factor F and resistivity index I respectively that Archie combined to provide the water saturation expression $S_w$ of equation (2). Certain logs have provided formation resistivity $R_t$ and porosity $\phi$. Water samples provide the best values for $R_w$. Standard practice is to measure rock sample resistivities $R_o$ and $R_t$ for a number of water saturations and to plot the logarithm of I versus the logarithm of $S_w$. Archie's equations assume such a logarithmic plot can be fit by a straight line with slope of $-n$.

Many core samples are, however, not homogenous and electrically isotropic. For such core samples, the Archie saturation exponent n will be strongly dependent on the direction the resistivity measurement is made. For example, a saturation exponent measured across permeability barriers within a core sample may be one and a half times as large as if it were measured parallel to the permeability barriers. This difference can have a large detrimental effect on the determination of hydrocarbon reserves derived from the calculated water saturation of equation (2). It is, therefore, an object of the present invention to determine resistivity of a core sample that is electrically anisotropic and to identify the degree of anisotropy changes as the brine saturation of the core sample changes so that an accurate water saturation can be calculated from equation (2).

SUMMARY OF THE INVENTION

The present invention is directed to a method for determining electrical anisotropy of a core sample from a subterranean formation.

The core sample is shaped in the form of a cylinder and a confining pressure applied. Electrical resistivity is determined in a plurality of directions through the core sample which are normal to the cylindrical axis of the core sample at a plurality of spaced-apart positions along such axis. These electrical resistivities are compared to identify the radial direction of any electrical anisotropy in the core sample.

More particularly, an initial fluid saturation is established within the core sample and the electrical resistivity determinations carried out. The fluid saturation is then altered a plurality of times and the electrical resistivity determinations repeated for each of such differing fluid saturations.

In carrying out the electrical resistivity determinations, the outer surface of the core sample is contacted with an array of electrodes at each of a plurality of spaced-apart positions along the length of the core sample, each of the arrays being in a plane normal to the axis and the electrodes in each of the arrays being equally spaced at an even number of positions about the outer surface of the core sample. A voltage is measured across each pair of electrodes that are spaced 180° apart about the core sample. The voltage measurements are utilized to determine the electrical resistivity of the core sample in a radial direction through the core sample normal to the axis between each pair of electrodes.

In shaping the core sample the core material is cut in the form of a cylinder such that its axis is at an angle to the bedding plane of the subterranean formation.

DESCRIPTION OF THE PREFERRED EMBODIMENT

Figure 1:
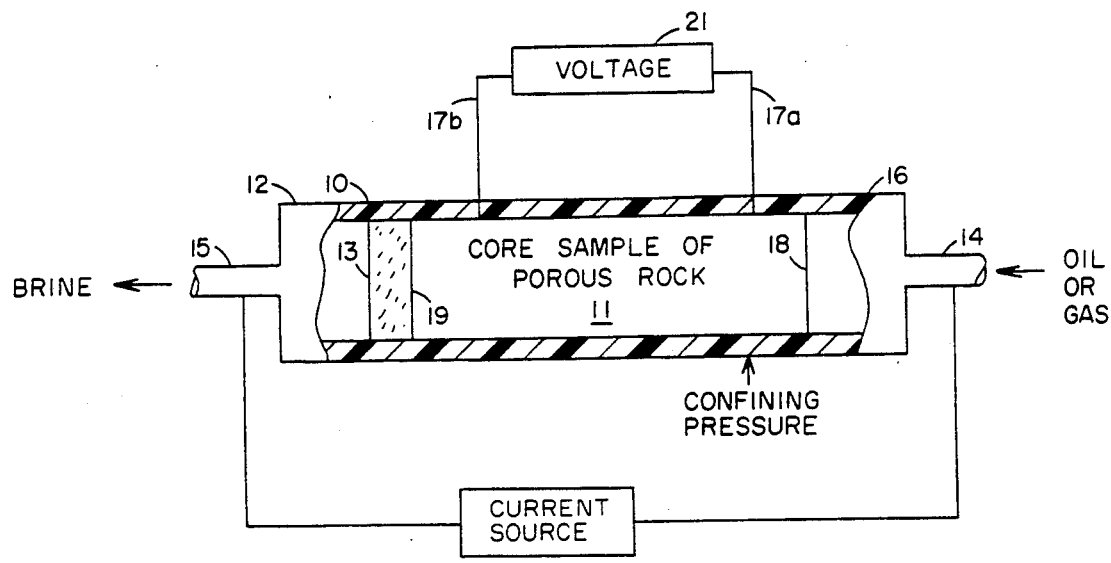
FIG. 1 illustrates prior art apparatus for carrying out resistivity determinations on core samples of subterranean formations.

A system that has been successfully used in carrying out linear resistivity determinations along a core sample from a subterranean formation is shown in FIG. 1 (prior art). A pressure sleeve 10, preferably natural or synthetic rubber, surrounds a cylindrical core sample 11 of a porous rock to be measured for resistivity at a plurality of fluid saturations. Positioned between the core sample 11 and end 12 of the pressure sleeve 10 is a porous member 13, which is permeable to a first fluid saturating the core sample, but is impermeable to a second fluid used to displace the first fluid from the core sample. The second, or displacing fluid, is immiscible with the first fluid saturating the core sample and is of different electrical conductivity. This first saturation fluid is the wetting fluid for the porous member 13, which by way of example, may be a ceramic plate or a membrane. Sleeve 10 is placed inside a suitable pressure vessel (not shown) that can be pressurized up to several thousand pounds per square inch. Typical of such pressure vessels are those described in U.S. Pat. Nos. 3,839,899 to McMillan; 4,688,238 to Sprunt et al; and 4,379,407 to Masse et al., the teachings of which are incorporated herein by reference. Through such a pressure vessel a pressure is applied to the sleeve 10 and hence to the porous rock 11. The pressure should be sufficient to eliminate any fluid annulus between the sleeve 10 and the surface of the core sample. A fluid inlet 14 and a fluid outlet 15 feed into the ends 16 and 12 respectively of the sleeve 10. Both inlet 14 and outlet 15 also serve as current conducting electrodes for passing current from a source 20 through the porous rock 11. A pair of voltage electrodes 17a and 17b penetrate sleeve 10 and make contact with the porous rock at spaced locations along the length of the porous rock. The voltage across the porous rock 11 between the electrodes 17a and 17b is measured by the unit 21.

The core sample of porous rock 11 is initially fully saturated, by way of example, with an electrically conducting fluid, such as salt water, and placed under confining pressure. A current is passed through the porous rock and a voltage along the length of the porous rock is measured between electrodes 17a and 17b. Such voltage measurement may be carried out in accordance with the teachings of U.S. Pat. No. 4,467,642 to Givens; U.S. Pat. No. 4,546,318 to Bowden and U.S. Pat. No. 4,686,477 to Givens et al, the teachings of which are incorporated herein by reference. The resistivity, or its reciprocal, conductivity, of the porous rock is determined using the measured voltage, the length, and the cross-sectional area of the core. A displacing fluid such as a nonconducting oil or gas, may then be forced through inlet 14 into end 18 of porous rock 11 to change the fluid saturation condition prior to the making of the next resistivity measurement.

Typical of such a resistivity determining system of FIG. 1 are those described in U.S. Pat. Nos. 4,907,448 and 4,926,128 to Givens and U.S. Pat. No. 4,924,187 to Sprunt et al.

Having now described a typical resistivity determination carried out in a single direction along the axial direction of a cylindrical core sample as shown in FIG. 1, the present invention of providing tensor components of resistivity, or conductivity, needed for interpreting electric logs of a subterranean formation with anisotropic properties by measuring and comparing resistivity in a plurality of radial directions through a cylindrical core sample of the formation and normal to its cylindrical axis will now be described. A transversely isotropic cylindrical core sample of the formation is cut so that the formation bedding plane is at an angle to the cylindrical axis of the core sample. The core sample is initially saturated with an electrically conducting fluid such as salt water, and placed within sleeve 10 under confining pressure representative of in-situ pressure. The core sample is contacted with an array of electrodes contained by sleeve 10 at each of a plurality of spaced-apart positions along the length of the core sample, such as electrode arrays A, B and C of FIG. 2 for example. Each such array A–C lies in a plane normal to the axis of the core sample and the electrodes in each array are equally spaced at an even number of positions about the sleeve 10.

Figure 2:
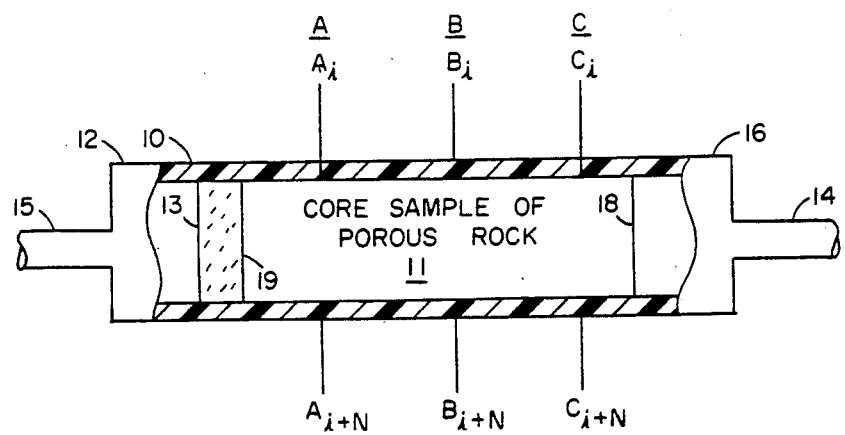
FIG. 2 illustrates apparatus employing electrode arrays for carrying out resistivity determinations on electrically anisotropic core samples of subterranean formations in accordance with the present invention.
Figure 3:
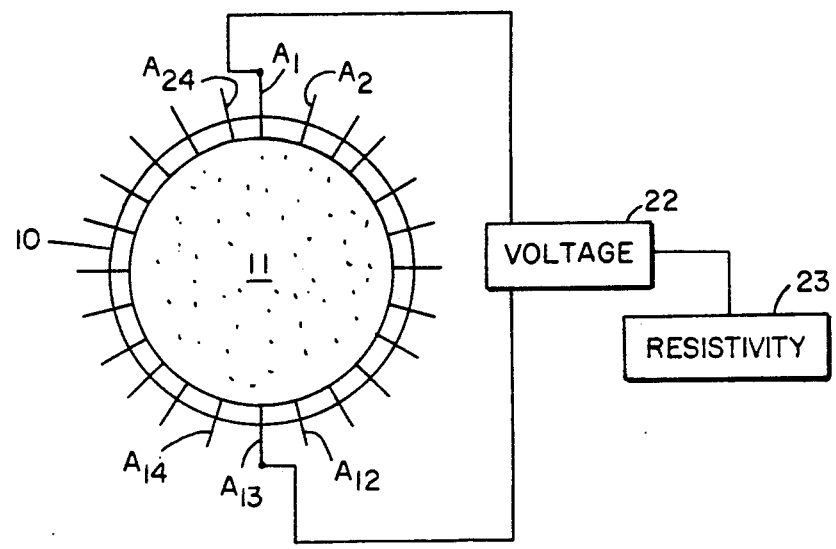
FIG. 3 is a cross-sectional view through the apparatus of FIG. 2 showing in detail one of the electrode arrays of FIG. 2.

FIG. 2 shows a pair of such electrodes $A_i$ and $A_{i+N}$ which are spaced-apart 180° about sleeve 10 (with i=1 to N). FIG. 3 is a cross-sectional view taken through the sleeve 10 and core sample 11 at the axial position of array A with 24 electrodes $A_1$–$A_{24}$ being shown (cross-sectioning of sleeve 10 being omitted for clarity). As can be seen in FIG. 3 there are 12 electrode pairs at 180° spaced-apart positions about sleeve 10 such as electrode pairs $A_1$ and $A_{13}$, $A_2$ and $A_{14}$–$A_{12}$ and $A_{24}$. A current is passed through core sample 11 and a voltage is measured across each of the $A_i$ an $A_{i+N}$, $B_i$ and $B_{i+N}$, and $C_i$ and $C_{i+N}$ electrode pairs spaced-apart 180° about the arrays A, B and C such as shown by voltage unit 22 across electrode pair $A_1$–$A_{13}$ for example. These voltages as well as a voltage measured along the axial length of the core sample by unit 21, such as shown in FIG. 1, are used by a resistivity unit 23 to determine the electrical resistivities of the core sample both along the core sample and in the plurality of radial directions through the core sample normal to core sample axis between the electrodes of each corresponding electrode pair. Following these measurements, the fluid saturation in the core sample may be altered any number of times with such measurements being repeated for each differing fluid saturation.

From the voltages measured normal to the axis of the core sample at a plurality of positions along the axis of the core sample the desired tensor components of resistivity, or conductivity, needed for interpreting electric logs of subterranean formations with anisotropic properties are determined. Core samples cut parallel and perpendicular to visible bedding planes at neighboring locations might be used to indicate and measure electrical anisotropy. However, such a procedure cannot be definitive because the samples might differ in their electrical properties regardless of how close together they resided in the original rock, and it would be difficult to obtain the same partial water saturations in each core sample for comparison measurements. A single cylindrical core sample cut with the bedding plane at an angle to the axis of the core sample as described above is utilized in accordance with the present invention to overcome such limitations.

Figure 4:
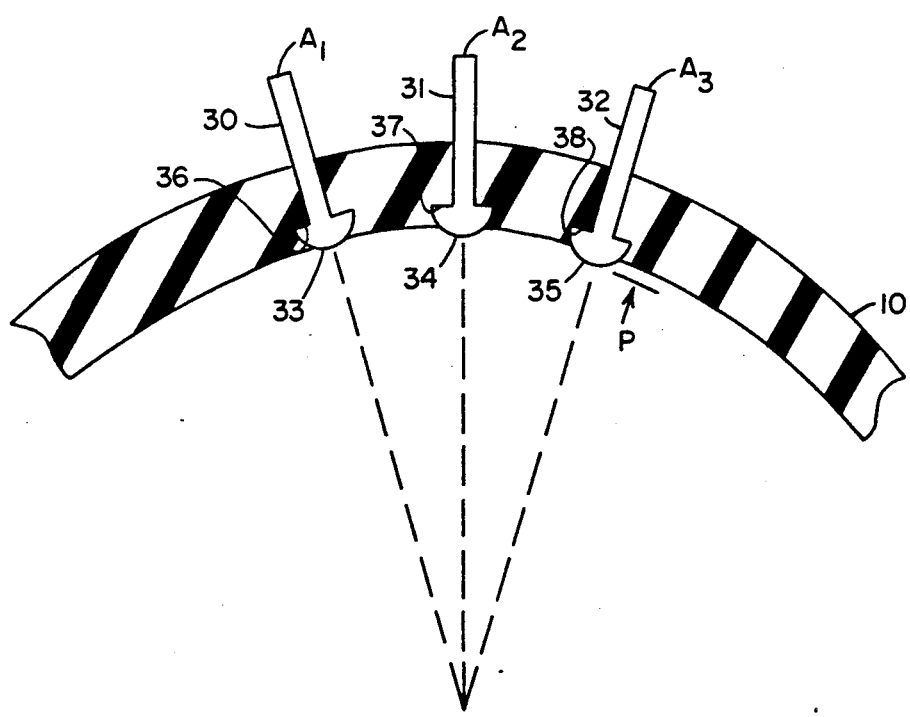
FIG. 4 illustrates one configuration for the electrodes of each of the electrode arrays of FIGS. 2 and 3.

Referring now to FIG. 4, there is shown a preferred configuration for the electrodes of each of the electrode arrays A–C. For purpose of example, electrodes $A_1$–$A_3$ are shown molded into a rubber sleeve 10 with cylindrical main body members 30–32 and spherical-like end members 33–35 for making contact with the outer surface of a core sample by extending outward from the inner surface of sleeve 10 by a distance d. As shown in FIG. 4, end members 33–35 are semispherical with recessed portions, or lips, 36–38, being normal to the outer surface of the cylindrical main body members 30–32. Such a semispherical end member provides for enhanced adhesion to the rubber sleeve 10.

While the foregoing has described a preferred embodiment of the present invention, it is to be understood that various modifications or changes may be made without departing from the spirit and scope of the invention as set forth in the appended claims.

We claim:

1. A method for determining electrical anisotropy of a core sample from a subterranean formation, comprising the steps of:
   a) shaping said core sample into the form of a cylinder,
   b) applying a confining pressure to said core sample,
   c) saturating said core sample with a fluid,
   d) passing a current through said fluid-saturated core sample,
   e) measuring voltages in a plurality of radial directions through said core sample which are normal to the cylindrical axis of said core sample at each of a plurality of spaced-apart positions along said axis,
   f) determining electrical resistivities in said plurality of radial directions through said core sample from said plurality of measured voltages, and
   g) comparing each of said determined electrical resistivities to identify the radial direction of any electrical anisotropy in said core sample.

2. The method of claim 1 wherein the step of measuring voltages comprises the steps of:
   a) establishing an initial fluid saturation within said core sample,
   b) measuring voltages in a plurality of radial directions through said core sample which ar normal to the cylindrical axis of said core at each of a plurality of spaced-apart positions along said axis at said initial fluid saturation, and
   c) altering said fluid saturation within said core sample a plurality of times and repeating the voltage measurements for each differing fluid saturation.

3. The method of claim 2 wherein the step of altering fluid saturation comprises the step of moving the fluid in said core sample in a direction parallel to said axis.

4. The method of claim 2 wherein the step of measuring voltages comprises the steps of:
   a) contacting the outer surface of said core sample with an array of electrodes at each of a plurality of spaced-apart positions along the length of said core sample, each of said arrays being in a plane normal to said axis and the electrodes in each of said arrays being equally spaced at an even number of positions about the outer surface of said core samples,
   b) measuring the voltage across each pair of electrodes that are spaced 180° apart about said core sample, and
   c) utilizing the voltage measurements across each pair of electrodes to determine the electrical resistivity of the core sample in a radial direction through said core sample normal to said axis between said pairs of electrodes.

5. The method of claim 1 wherein the step of shaping said core sample is carried out by cutting the core such that the cylindrical axis of said core sample is at an angle to the bedding plane of said subterranean formation.

6. A method for determining electrical anisotropy of a core sample from a subterranean formation, comprising the steps of:
   a) shaping said core sample into the form of a cylinder with the cylindrical axis at an angle to the bedding plane of the subterranean formation,
   b) applying a confining pressure to said core sample,
   c) saturating said core sample with a first fluid,
   d) passing a current through said fluid-saturated core sample,
   e) measuring voltages in a plurality of radial directions through said core sample which are normal to the cylindrical axis of said core sample at each of a plurality of spaced-apart positions along said axis,
   f) determining electrical resistivities in said plurality of radial directions through said core sample from said plurality of measured voltages,
   g) comparing each of said determined electrical resistivities to identify the radial direction of any electrical anisotropy in said core sample, and
   h) displacing at least a portion of said first fluid with a second fluid of differing electrical conductivity and repeating steps (d) to (g).

7. The method of claim 6 wherein said first fluid is electrically conductive and said second fluid is electrically non-conductive.

8. The method of claim 6 wherein said first fluid is electrically non-conductive and said second fluid is electrically conductive.

* * * * *